(12) United States Patent
Xia

(10) Patent No.: US 8,653,284 B2
(45) Date of Patent: *Feb. 18, 2014

(54) LACTONE STABILIZING COMPOSITIONS

(75) Inventor: Jusong Xia, Moore, SC (US)

(73) Assignee: Milliken & Company, Spartanburg, SC (US)

( * ) Notice: Subject to any disclaimer, the term of this patent is extended or adjusted under 35 U.S.C. 154(b) by 405 days.

This patent is subject to a terminal disclaimer.

(21) Appl. No.: 12/562,456

(22) Filed: Sep. 18, 2009

(65) Prior Publication Data

US 2010/0010124 A1      Jan. 14, 2010

Related U.S. Application Data

(63) Continuation of application No. 12/122,961, filed on May 19, 2008, now Pat. No. 7,601,853, which is a continuation of application No. 11/016,171, filed on Dec. 17, 2004, now Pat. No. 7,390,912.

(51) Int. Cl.
*C07D 305/12* (2006.01)
*C08K 5/15* (2006.01)

(52) U.S. Cl.
USPC ............................... 549/307; 524/111

(58) Field of Classification Search
USPC ............................... 549/307; 524/111
See application file for complete search history.

(56) References Cited

U.S. PATENT DOCUMENTS

| | | | |
|---|---|---|---|
| 4,325,863 A | 4/1982 | Hinsken et al. | |
| 4,338,244 A | 7/1982 | Hinsken et al. | |
| 5,175,312 A | 12/1992 | Dubs et al. | |
| 5,367,008 A * | 11/1994 | Nesvadba | 524/111 |
| 5,369,159 A | 11/1994 | Nesvadba | |
| 5,428,162 A | 6/1995 | Nesvadba | |
| 5,516,920 A | 5/1996 | Nesvadba et al. | |
| 5,607,624 A | 3/1997 | Nesvadba et al. | |
| 5,883,165 A * | 3/1999 | Krohnke et al. | 524/111 |
| 6,417,358 B1 | 7/2002 | Tinkl et al. | |
| 6,521,681 B1 | 2/2003 | Zingg et al. | |
| 7,390,912 B2 | 6/2008 | Xia | |
| 7,601,853 B2 | 10/2009 | Xia | |

FOREIGN PATENT DOCUMENTS

| | | |
|---|---|---|
| FR | 2 750 701 A | 1/1998 |
| WO | WO 00/23849 | 4/2000 |
| WO | WO 02/074847 A1 | 9/2002 |

OTHER PUBLICATIONS

Auger, M. et al. *Bulletin de la Société Chimique de France* 1970, 4024-4030.
Jurd, L. *Aust J Chem* 1978, 31, 347-352.
Foote, C.S. et al. *JACS* 1973, 95:2, 586-88.

* cited by examiner

*Primary Examiner* — Nizal Chandrakumar
(74) *Attorney, Agent, or Firm* — Robert M. Lanning

(57) ABSTRACT

This invention provides a novel class of compounds and compositions and synthetic methods related to lactone antioxidant 3-arylbenzofuranones. The compounds may be useful to prevent yellowing and deterioration of organic materials preferably polymers, such as polyurethane foams as one example. The lactone antioxidants may be polymeric, and may also be liquid or paste in physical form at room temperature. Although it is not necessary for its stabilizing properties, the compositions may, in some species, bear one or more reactive primary OH groups on the polymer chains. The chains may also contain oligomeric oxyalkylene ether and aliphatic ester functional groups, in one embodiment of the invention.

8 Claims, No Drawings

LACTONE STABILIZING COMPOSITIONS

This application is a continuation of, and claims the benefit of the filing date of, U.S. patent application Ser. No. 12/122,961, filed on May 19, 2008 and issued on Oct. 13, 2009 as U.S. Pat. No. 7,601,853, which application is a continuation of and claims the benefit of the filing date of U.S. patent application Ser. No. 11/016,171, filed on Dec. 17, 2004 and issued on Jun. 24, 2008 as U.S. Pat. No. 7,390,912, each of which is hereby incorporated by reference.

FIELD OF THE INVENTION

The present invention relates to compositions comprising an organic material, such as a polymer, and an oligomeric lactone for use as a stabilizers. The inventive compositions may be employed for stabilization of organic materials against oxidative, thermal, or light-induced degradation. The invention is directed to novel oligomeric lactones.

BACKGROUND OF THE INVENTION

Various compositions are known that function to stabilize organic materials against oxidative, thermal or light-induced degradation. Such stabilization compositions may have broad applications in thermoplastics such as polyolefin, thermoset resins such as polyurethanes, and coating formulations. One problem with polyurethane foams, for example, is that such foams tend to yellow after a certain period of time. Yellowing of foam products is undesirable. Such yellowing may be caused by NOx gas fading or UV radiation.

U.S. Pat. Nos. 4,325,863 and 4,338,244 to Hinsken disclose 3-aryl benzofuran-2-ones and their dimers as new class of stabilizers in various organic polymers such as polyolefins, polyurethanes and polyesters.

U.S. Pat. Nos. 5,367,008 and 5,369,159 and 5,428,162 to Nesvadba disclose the preparation of various 3-(alkoxyphenyl)benzofuran-2-ones and 3-(acyloxyphenyl)benzofuran-2-one derivatives, for use as polymer stabilizers.

The prior art provides a number of relatively non-reactive, solid stabilizers. Solids are difficult to use in manufacturing processes. Solids provide difficulties in handling, migration, fogging, and blooming.

New and more effective stabilizing compounds are needed in the industry. This invention provides such compounds.

DETAILED DESCRIPTION OF THE INVENTION

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention.

This invention provides a novel class of compounds and compositions and synthetic methods. In one aspect of the invention, the compositions may comprise polymeric or oligomeric lactone antioxidants, such as poly(oxyalkylene) chain(s) substituted 3-arylbenzofuranones or poly(caprolactone) chain(s) substituted 3-arylbenzofuranones. The inventive lactone antioxidants may be polymeric or oligomeric, which may be liquid or pastes in nature at room temperature. In many applications, liquid or paste forms of such compounds provide a remarkable and surprising advantage. Although it may not be necessary for its stabilizing properties, the compositions may bear one or more reactive primary —OH groups on the polymer chains. For some applications, the terminal group(s) of the polymer chain(s) is not believed to be critical with regard to the functioning of the polymeric lactones in stabilizer compositions. The chain(s) may also contain oxyalkylene ether and aliphatic ester functional groups or radicals.

The inventive liquid lacones polymeric/oligomeric chains may contain oxyalkylene segments (such as ethylene oxide and/or propylene oxide, etc, and the EO/PO ratio can be designed as such to achieve desired hydrophilic and/or hydrophobic properties) and/or aliphatic ester segments (hydrophobic). This affords the opportunity to "tune" the lactone antioxidants for desirable compatibility in various media such as thermosets (polyurethane), thermoplastics (PET, PP, PS, PC and the like), wax, aqueous systems (liquid hand soap, detergents, sunscreens, fabric softeners etc. consumer products), and coatings.

Lactones bearing unique polymeric/oligomeric chains may also be comprised of specific combination of EO/PO/aliphatic esters that are compatible with most of the above-mentioned applications. The liquid nature of the inventive polymeric lactones provides ease of handling during the application process. That is, the compositions may desirably be liquids or pastes at room temperature, making it much easier to apply the compositions in manufacturing processes. And the polymeric/oligomeric nature of the inventive lactones provides higher molecular weight and better compatibility with application media, thus is less volatile, and less prone to migrate, bloom and plate-out.

In some applications, primary hydroxy groups are present on the inventive lactone molecules. These structures offer superior reactivity in polyurethane, PET and coating systems. Thus the polymeric lactone molecules may be chemically attached on to the application media if such is desirable. The inventive polymeric UV absorbers may solve or mitigate migration, leaching, fogging, plate-out, and extraction problems, each of which is highly undesirable.

The inventive polymeric lactone antioxidants 3-arylbenzofuranones, when used along with other additives such as UV absorbers, other antioxidants, and light stabilizers, may significantly reduce the gas fading (NOx) and UV radiation induced yellowing of white polyurethane foam. The compositions may be provided in liquid form, and are reactive into the foam, which is a significant advantage. That is, these compositions are truly polymeric or oligomeric, having in some applications polyoxyalkylene and aliphatic polyester block copolymer/oligomer chains.

The inventive lactone stabilizers may be liquid and polymeric. They may provide ease of handling, processing and metering. The inventive lactone stabilizers may bear primary —OH groups at the end of polymer chains. They may be completely reactive in polyurethane, coatings, PET, and polycarbonate applications if such is desirable. They may provide antioxidant functions to resist undesirable extraction, migration, fogging, and leaching out of the polymer matrix.

In one application, the compounds of the invention may be described as follows:

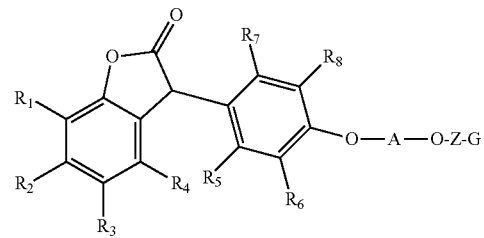

wherein:

$R_1$-$R_8$ are each independently selected from the group consisting of H, F, Cl, Br, I, $C_1$-$C_{20}$ alkyls, $C_1$-$C_{20}$ cycloalkyls, $C_1$-$C_{20}$ alkoxy groups, $C_7$-$C_{20}$ phenylalkyls, and phenyl groups;

A is a $C_2$-$C_{20}$ alkylene oxide group or a divalent oligomeric oxyalkylene radical;

Z is a $C_2$-$C_{20}$ alkyl or a divalent oligomeric ester radical; and

G is an end group and is selected from the group consisting of H, $C_1$-$C_{10}$ alkyls, alkyl carbonyls and aryl carbonyls.

The composition "A" recited above may comprise a divalent oligomeric oxyalkylene radical, which may provide the structure:

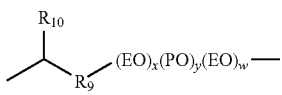

wherein:

EO comprises ethylene oxide or a derivative thereof;

PO comprises propylene oxide or a derivative thereof;

$R_9$ comprises a divalent $C_1$-$C_{20}$ alkyl radical;

x, y and w are independently selected from the group consisting of: zero and positive integers or fractions between 1 and 20; wherein x+y+w is equal or greater than 1; and wherein $R_{10}$ comprises H or a $C_1$-$C_{20}$ alkyl group.

Furthermore, the Z group may be comprised of a divalent oligomeric ester radical, having the structure:

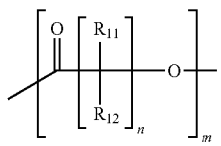

wherein:

$R_{11}$ and $R_{12}$ are independently selected from H or $C_1$-$C_{10}$ alkyl groups;

n comprises an integer between 1 and 10; and m comprises any positive integer or fraction between 1 and 20.

In another embodiment, a compound of the invention may also be represented by the formula:

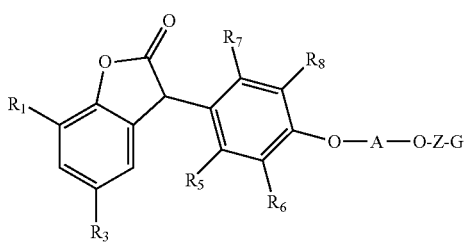

wherein $R_1$, $R_3$, $R_5$-$R_8$, A, Z and G are as defined above.

Still in another embodiment, a compound of the invention may also be represented by the formula:

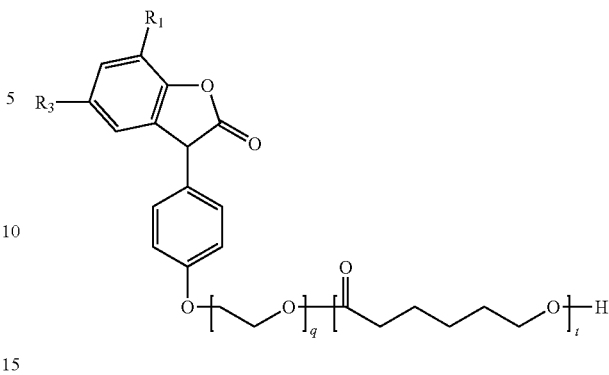

wherein:

$R_1$, and $R_3$ are as defined above, and q is a positive integer between 1 and 20, and t is a positive integer between 0 and 20, and wherein q+t is equal to or greater than 3.

Further specifically, a compound of the invention may be represented by the formula:

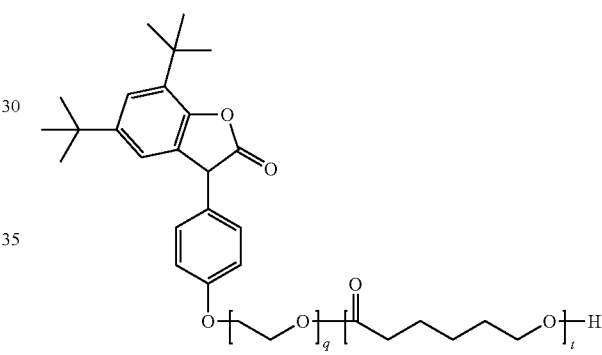

wherein q and t are as defined above.

The compounds according to the invention may be effective antioxidants when used alone or in combination with other conventional antioxidants, for stabilizing organic materials, for example for coatings and a large number of polymers. For all applications in which a liquid, oligomeric and non-migration properties are highly desirable, the inventive compounds afford advantages over conventional lactone antioxidants. These polymers may be polyurethane, polyolefin, polycarbonate, polyamide, epoxyl resin, polyethers such as polyethylene glycol, polypropylene glycol or polytetramethylene glycol, and the like.

The stabilizing compositions are incorporated into the organic material by the conventional methods, for example in any desired phase during the manufacture of shaped products. They can, for example, be mixed in the form of a liquid, a paste, a powder with other materials, suspensions or emulsions or solutions into the polymer, which can be in the form of a powder, melt, solution, suspension or emulsion.

In stabilizing polyurethane foam in particular, the inventive compounds can be used with the following classes of additives:

Class A: Benzotriazoles are (in general) those compounds that conform to the structure represented as the following:

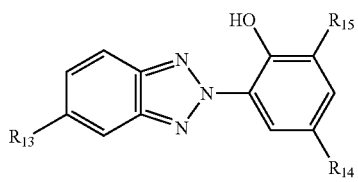

wherein $R_{13}$, $R_{14}$, and $R_{15}$ are independently selected from hydrogen, a group having a formula $C_aH_bN_cO_dS_e$ wherein a, b, c, d, and e are from 0 to 30, and halogen.

Class B: Hindered phenols or BHT derivatives, and related compounds typically conform to the structure of the following:

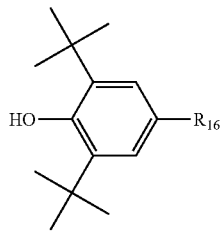

wherein $R_{16}$ is selected from the group consisting of hydrogen, a group having a formula $C_aH_bN_cO_dS_e$ wherein a, b, c, d, and e may be from 0 to 30, and halogen.

Class C: Secondary diphenylamines may conform to the structure of the following

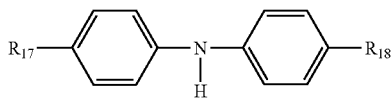

wherein $R_{17}$ and $R_{18}$ are individually selected from the group consisting of hydrogen, a group having a formula $C_aH_bN_cO_dS_e$ wherein a, b, c, d, and e are from 0 to 30, and halogen.

Class D: other conventional Lactone-based antioxidants may include those compounds that conform to the structure of the following:

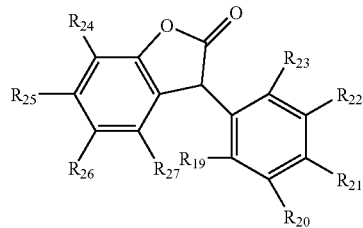

wherein $R_{19}$ to $R_{27}$ are individually selected from the group consisting of hydrogen, a group having a formula $C_aH_bN_cO_dS_e$ wherein a, b, c, d, and e are from 0 to 30, and halogen.

Several examples of the synthesis and application of the invention are shown below, in written form of Examples, and in data produced for Tables.

Synthetic Examples of the Invention

Example 1

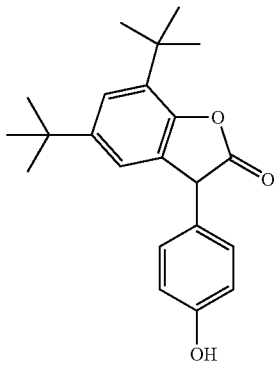 [SMILES: CC(C)(C)c1cc2c(c(C(C)(C)C)c1)OC(=O)C2c1ccc(O)cc1]

Two hundred seventy four grams of 2,4-di-tert-butylphenol, 165 g of 4-hydroxymandelic acid and 530 ml of acetic acid were combined in a two liter three neck round bottom flask equipped with a temperature probe, stirring apparatus and condenser. The mixture was heated to 95° C., at which, 2.6 g of methanesulfonic acid were added. The reaction was allowed to proceed at 95° C. for three hours. After cooling to room temperature and sitting overnight, the precipitated product was collected via filtration. This filtercake was washed several times with acetic acid until the precipitate was white. After drying in a 50° C. oven, 175 g of 5,7-di-tert-butyl-3-(4-hydroxyphenyl)benzofuran-2-one product having a melting point of 189-191° C. were obtained.

Example 2

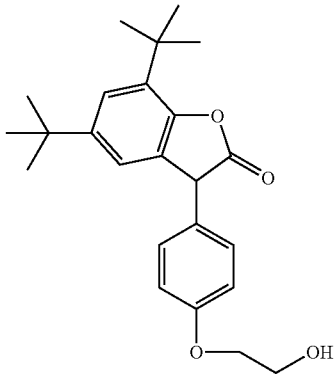 [SMILES: CC(C)(C)c1cc2c(c(C(C)(C)C)c1)OC(=O)C2c1ccc(OCCO)cc1]

In a three liter three neck round bottom flask, a solution of 32.4 g of sodium hydroxide in 810 ml of water was formed. With stirring, 91.6 g of 5,7-di-tert-butyl-3-(4-hydroxyphenyl)benzofuran-2-one were added and the mixture heated to 80° C. under a nitrogen atmosphere. Once at 80° C., 27 ml of 2-chloroethanol were added and the reaction held at 80° C. for two hours. After cooling to room temperature, a solution of 99 ml of concentrated hydrochloric acid in 1251 ml of water was added and the reaction held again at 80° C. for an additional hour. Once cooled to room temperature, the liquid was decanted and the remaining solid dissolved in 500 ml of methylene chloride. This solution was washed once with 300 ml of water. After drying the methylene chloride layer over magnesium sulfate and stripping, 92.6 g of 5,7-di-tert-butyl-3-[4-(2-hydroxy-ethoxy)-phenyl]benzofuran-2-one, a light yellow solid remained. This solid can be further recrystallized from ethanol/water.

Example 3

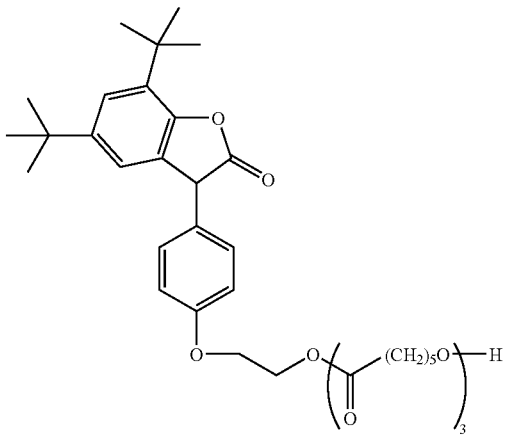

Fifteen grams of 5,7-di-tert-butyl-3-[4-(2-hydroxy-ethoxy)-phenyl]benzofuran-2-one, 13.5 g of ε-caprolactone and 0.3 g of 50% hypophosphorous acid were charged to a 100 ml three neck flask. Under a nitrogen atmosphere, the mixture was heated to 100° C. and held for three hours. Twenty four grams of viscous liquid product having a light yellow color were obtained.

Example 4

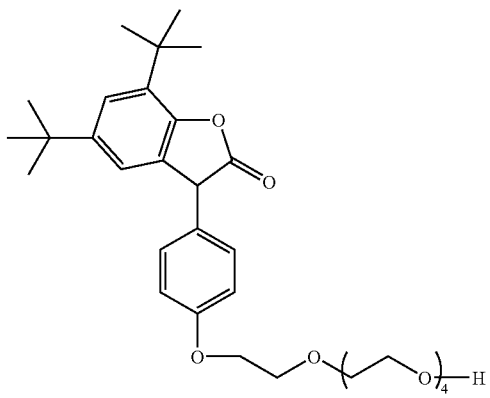

Three hundred grams of 5,7-di-tert-butyl-3-(4-hydroxyphenyl)benzofuran-2-one, 500 g of toluene and 3 g of lanthanum phosphate catalyst were charged into an autoclave. The reaction mixture was purged several times with nitrogen gas (to a pressure of 60 PSIG) and finally pressurized to 5 PSIG of nitrogen. After heating the autoclave to 121° C., ethylene oxide was added to the reaction mixture until the pressure in the reactor reached 60 PSIG. After the pressure dropped to 30 PSIG due to consumption of ethylene oxide, more ethylene oxide was added to the reactor in the same fashion as previously described until a total of 192 g of ethylene oxide had been added. Afterwards, the reaction mixture was post-cooked for a total of 30 minutes. Toluene was removed via vacuum stripping yielding 472 g (96%) of a light yellow viscous liquid.

Article Production and Performance Testing for Inventive Liquid Polymeric Lactone Antioxidants a) Polyether Foam Article Formation The inventive lactone antioxidants were incorporated with or without other additives to produce (in one particular embodiment of the invention) polyurethane foam in accordance with the following formulation and procedure:

| Component | Amount |
| --- | --- |
| F3022 Polyol (from Bayer) | 100 grams |
| Water | 4.53 ml |
| DABCO 33LV (catalyst, from Air Products) | 0.15 ml |
| DABCO T10 (catalyst) | 0.32 ml |
| L520 Silicone (from Crompton) | 1.0 mL |
| 80/20 Toluene diisocyanate (Bayer, 112 index) | 49.0 ml |
| Reactint ® Blue X3LV | as noted |
| Inventive Polymeric Lactone Antioxidants | as noted |
| Additive from Class A Tinuvin ® 326 | as noted |
| Additive from Class B Irganox ® 1135 | as noted |
| Additive from Class C Irganox ® 5057 | as noted |
| Additive from Class D Irganox ® HP 136 | as noted |

Upon mixture within a reaction vessel, the reaction created a "health" bubble (indicating gelation and blowing balance), and the vessel was then exposed to 160° C. (generated within a conventional oven to simulate actual heat history encountered on an industrial production level) for about 3 minutes allowing the material to cure to form a foam bun. The resultant foam buns were then analyzed for performance, as discussed in details below.

b) Performance Characteristics of Polyether Foams Including Inventive Polymeric Liquid Lactone Antioxidants The white foams made in accordance with formulation and process as described in Section a), were all tested for standard foam performance, in terms of rise time, tack time, and bun height, and compared with the control polyether foams either made with conventional commercial lactone antioxidant Irganox® HP 136 or made without additive. Measurements within 5% of the control are considered acceptable for the finished foam product. The measurements are summarized in Table 1.

TABLE 1

Foam Performance of Inventive or Comparative Lactone Antioxidants

| Sample Foam # | Additive (Mw) | Loading (php) | Rise Time (minutes) | Tack Time (minutes) | Bun Height (mm) |
| --- | --- | --- | --- | --- | --- |
| A1 | N/A | N/A | 1.50 | 3 | 226 |
| A2 | HP-136 (Mw 350.7) | 1.0 | 1.54 | 3 | 230 |
| A3 | Example 3 (Mw 724) | 1.0 | 1.52 | 3 | 234 |
| A4 | Example 3 (Mw 724) | 2.0 | 1.52 | 3 | 228 |
| A5 | Example 4 (Mw 558) | 1.0 | 1.50 | 3 | 232 |

TABLE 1-continued

Foam Performance of Inventive or Comparative Lactone Antioxidants

| Sample Foam # | Additive (Mw) | Loading (php) | Rise Time (minutes) | Tack Time (minutes) | Bun Height (mm) |
|---|---|---|---|---|---|
| A6 | Example 4 (Mw 558) | 1.6 | 1.55 | 3 | 233 |

Additionally, the foams produced exhibited good resiliency and densities measured at about 1.5 pounds per cubit foot. Thus, the inventive polymeric lactone antioxidants provide acceptable polyurethane foam articles as compared with control samples.

c) Extraction Measurements From Polyurethane Foams

The polyurethane foams produced in above Section b) were analyzed for extraction levels using the following method. The extraction test involved cutting 1 gram of the cured foam from the center of the sample and post-curing the cut foam for another 20 minutes at 160° C. in a glass jar. After cooling to room temperature, 75 grams of methanol were then added to the glass jar that was then capped for 1 hour. The foam was then removed and the extract solution was analyzed to detect the percentages of the lactone antioxidants being extracted out. The results are summarized in Table 2.

TABLE 2

Foam Extraction Tests of Inventive or Comparative Lactone Antioxidants

| Sample Foam # | Additive (Mw) | Loading (php) | Extraction (%) |
|---|---|---|---|
| A1 | N/A | N/A | Not detectable |
| A2 | HP-136 (Mw 350.7) | 1.0 | >96 |
| A3 | Example 3 (Mw 724) | 1.0 | <5 |
| A4 | Example 3 (Mw 724) | 2.1 | <5 |
| A5 | Example 4 (Mw 558) | 1.0 | <5 |
| A6 | Example 4 (Mw 558) | 1.6 | <5 |

Based on the molecular weight of these additives, 1.0 php of HP-136 is molar equivalent to 2.1 php of inventive additive from Example 3, and 1.6 php of inventive additive from Example 4. As suggested from Table 2, the inventive liquid polymeric lactone antioxidants provide significant improvement in the foam extraction test, comparing to comparative examples such as commercial product HP-136.

d) Protection of Colorants from Thermal Discoloration in Polyurethane Foam

Liquid polymeric colorant Reactint® Blue X3LV (available from Milliken Chemical) is widely used for the coloration of polyurethane foam, and is known to be prone to thermal discoloration during foam article formulation. Thus, the blue foams were made in the presence of 1 php Blue X3LV with or without inventive and comparative lactone antioxidants, in accordance with formulation and process similar to those as described Section a), with the exception that after the reaction created a "health" bubble (indicating gelation and blowing balance), the vessel was then exposed to 185° C. (generated within a microwave oven to simulate actual heat history encountered on a large industrial production environment) for about 10 min before it was exposed to 160° C. (generated by a conventional oven) for 3 minutes to cure the foam bun. The foam buns were sliced in half, and then compared reading at the center of the foam bun (usually where the discoloration occurs) in CMC for delta E with the reading at the outer section of the foam bun (usually where no discoloration occurs). The results are summarized in Table 3.

TABLE 3

Stabilize Reactint® Blue X3LV from Thermal Discoloration during Polyurethane Foam Formation

| Sample Foam # | Additive | Mw | Loading (php) | Delta E | Observation at the center of foam bun |
|---|---|---|---|---|---|
| A7 | Control (X3LV only) | n/a | n/a | 4.6 | some yellowing or color loss |
| A8 | HP-136 | 350 | 1 | 1.8 | No color change |
| A9 | Example 3 | 724 | 1 | 1.9 | No color change |
| A10 | Example 4 | 558 | 1 | 2.4 | Trace yellowing or color loss |
| A11 | Example 4 | 558 | 1.5 | 1.4 | No color change |

The data in Table 3 suggested that the inventive polymeric liquid lactone antioxidants were very effective in stabilization of polymeric colorants such as Blue X3LV from thermal degradation during the polyurethane foam production process.

e) Protection of Pure Polyol from Thermal Degradation/Yellowing During Polyurethane Foam Formation Polyols are known to be very prone to oxidation. In order to retain the physical and chemical properties, almost all commercial polyols are protected with conventional hindered phenol antioxidants for storage and transportation. One major side effect of the hindered phenols is that they cause discoloration/yellowing during polyurethane article formation and when exposed to exhaust gas (NOx). An antioxidant which can effectively protect the intergraty of polyols without causing polymers such as polyurethane foam yellowing and compatible with polyols is highly desired. In order to test the effectiveness of the inventive polymeric lactone antioxidants, the white foams (without adding any colorant) were made using pure polyol (no conventional antioxidant package presence) with or without inventive and comparative lactone antioxidants, in accordance with formulation and process similar to those as described Section a), with the exception that after the reaction created a "health" bubble (indicating gelation and blowing balance), the vessel was then exposed to 185° C. (generated within a microwave oven to simulate actual heat history encountered on a large industrial production environment) for about 10 min before it was exposed to 160° C. (generated by a conventional oven) for 3 minutes to cure the foam bun. The foam buns were sliced in half, and then compared reading at the center of the foam bun (usually where the discoloration occurs) in CMC for delta E with the reading at the outer section of the foam bun (usually where no discoloration occurs). The results are summarized in Table 4.

TABLE 4

Performance of Compositions in Stabilizing Pure Polyol from Thermal Degradation/Yellowing During PU Foam Formation

| Sample Foam # | Additive | Mw | Loading (php) | Delta E | Observation at the foam center |
|---|---|---|---|---|---|
| A12 | Control (Pure polyol) | n/a | n/a | 48.1 | Very yellow |
| A13 | HP-136 | 350 | 0.1 | 1.1 | No color change |
| A14 | HP-136 | 350 | 1 | 4.2 | No color change |
| A15 | Example 3 | 724 | 0.1 | 1.5 | No color change |
| A16 | Example 3 | 724 | 1 | 2.3 | No color change |
| A17 | Example 4 | 558 | 0.1 | 2.6 | No color change |
| A18 | Example 4 | 558 | 1 | 2.8 | No color change |

Thus, the inventive polymeric liquid lactone antioxidants are very effective in stabilizing pure polyols from thermal degradation.

f) Protection of Polyurethane Foam Made with Pure Polyols from Gas Fading

In order to test the effectiveness of the inventive polymeric lactone antioxidants in stabilizing the pure polyols from gas (NOx) fading and comparing the performance with commonly used conventional hindered phenol antioxidant package, the white foams (without adding any colorant) were made using pure polyol (no conventional antioxidant package presence), as well as regular polyols (with the conventional stabilizer package presences) with or without inventive and comparative lactone antioxidants, in accordance with formulation and process similar to those as described in Section a). After curing, the foam buns were sliced in half, and small pieces of foam samples (diameters of 10 cm×5 cm×2 cm) were cut from the center of each foam bun. These foam samples were all tested under NOx gas chamber (NOx concentration is 1 ppm) for discoloration at different exposure time. Those foam samples exposed to different amounts of time in NOx chamber testing were then compared reading in CMC for delta E with respected unexposed foam samples. The results are summarized in Table 5.

TABLE 5

Performance of Compositions in Stabilizing PU Foam Formation Made with Pure Polyol from Gas Fading

| Sample Foam # | Additive | Mw | Loading (php) | Delta E | Observation of exposed foam sample |
|---|---|---|---|---|---|
| A19 | Control 1 (regular polyol) | n/a | n/a | 39.4 | Yellow-brownish |
| A20 | Control 2 (Pure polyol) | n/a | n/a | 13.4 | Slight yellow |
| A21 | HP-136 | 350 | 0.1 | 21.5 | Slight yellow |
| A22 | Example 3 | 724 | 0.1 | 16.7 | Slight yellow |
| A23 | Example 4 | 558 | 0.1 | 17.1 | Slight yellow |
| A24 | Example 4 | 558 | 0.4 | 17.5 | Slight yellow |

It is thus clear that the inventive liquid polymeric lactone antioxidants are superior to conventional hindered phenol antioxidant package in stabilizing polyol from NOx fading.

g) Reduction of Discoloration in White Polyurethane Foam

Several white foams made in accordance with formulation and process as described in Section a), in the presence of unique anti-discoloration additive packages consists of a UV absorber selected from Class A, a phenolic antioxidant from Class B, a secondary amine antioxidant from Class C and a lactone antioxidant from Class D. The inventive liquid polymeric lactone antioxidants are used in this unique additive package to replace the commercial antioxidant Irgnox® HP-136 which is solid and/or may not thoroughly miscible with polyols. The foams are made with the inventive additive packages, as well as commercially available additive packages, the foam buns are then sliced in half and 2 sets of small pieces of foam samples (diameters of 10 cm×5 cm×2 cm) were cut from the center of each foam bun. One set of these foam samples were tested under Xenon lamp and compared the performance against UV discoloration (Xenon lamp test according to AATCC Test No. 16-1999) and Another set of samples were tested under NOx gas chamber (NOx concentration is 1 ppm) for discoloration at different exposure time (gas fading test as described in AATCC Test No. 23-1999). Those foam samples exposed to different amounts of time under UV lamp or in the NOx chamber were then compared reading in CMC for delta E with respected unexposed foam samples. The inventive synergistic additive composition packages are listed in Table 6. Also included in Table 6 as comparatives, are control (with no additive) and commercially available additive packages B-75 (Ciba), CS-31 (Crompton) and LS-1 (Ortegol), which are current best commercial products in polyurethane industry for stabilization of white polyurethane foams.

TABLE 6

Additive Compositions and Loadings in Foam Formulation

| Additive package | Class A (php) | Class B (php) | Class C (php) | Lactone AO (php) |
|---|---|---|---|---|
| AA | Tinuvin 326 (1.5) | Irgnox 1135 (0.33) | Irgnox 5057 (0.50) | HP-136 (0.57) |
| BB | Tinuvin 326 (1.5) | Irgnox 1135 (0.33) | Irgnox 5057 (0.50) | Example 3 (1.18) |
| CC | Tinuvin 326 (1.5) | Irgnox 1135 (0.33) | Irgnox 5057 (0.50) | Example 4 (0.57) |
| DD | Tinuvin 326 (1.5) | Irgnox 1135 (0.33) | Irgnox 5057 (0.50) | Example 4 (1.16) |
| GG | Tinuvin B75 (commercially available from Ciba), loading @ 3.0 php | | | |
| HH | CS-31 (commercially available from Crompton), loading @ 3.0 php | | | |
| JJ | LS-1 (commercially available from Goldschmidt), loading @ 3.0 php | | | |
| Control | 0 | 0 | 0 | 0 |

Lightfastness and gas fade test results for the inventive and comparative sample foams are summarized in Table 7.

TABLE 7

Test Results for Inventive and Comparative Additive Packages

| Sample Foam # | Additive Package | Lightfastness delta E (13 hrs) | Gas Fade delta E (2 hrs) | Gas Fade delta E (4 hrs) |
|---|---|---|---|---|
| A25 | Control (N/A) | 34.6 | 34.2 | 56.2 |
| A26 | AA | 8.7 | 8.8 | 21.2 |
| A27 | BB | 7.7 | 10.8 | 27.6 |
| A28 | CC | 11.6 | 11.8 | 33.4 |
| A29 | DD | 10.0 | 11.3 | 23.5 |
| A30 | GG | 15.8 | 34.1 | 82.5 |
| A31 | HH | 18.2 | 51.4 | 53.1 |
| A32 | JJ | 13.5 | 37.3 | 53.6 |

Clearly, the inventive additive packages containing the inventive liquid polymeric lactone antioxidants exhibited among the best overall performance against discoloration of UV exposure and gas fade, comparing to state-of-the-art commercial additive packages such as GG, HH and JJ.

It is understood by one of ordinary skill in the art that the present discussion is a description of exemplary embodiments only, and is not intended as limiting the broader aspects of the present invention. The invention is shown by example in the appended claims.

What is claimed is:

1. A compound having the structural formula:

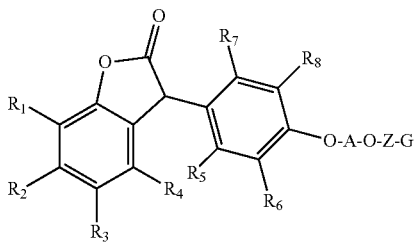

wherein:
$R_1$ and $R_3$ are independently selected from the group consisting of H, $C_1$-$C_{20}$ alkyls, $C_1$-$C_{20}$ cycloalkyls, $C_1$-$C_{20}$ alkoxy groups, $C_7$-$C_{20}$ phenylalkyls, and phenyl groups;
$R_2$ and $R_4$ are each hydrogen;
$R_5$, $R_6$, $R_7$ and $R_8$ are independently selected from the group consisting of H $C_1$-$C_{20}$ alkyls, and $C_1$-$C_{20}$ alkoxy groups;
A is a $C_2$-$C_{20}$ alkylene oxide group or a divalent oligomeric oxyalkylene radical;
Z is a $C_2$-$C_{20}$ alkyl or a divalent ester radical; and
G is an end group selected from the group consisting of H, $C_1$-$C_{10}$ alkyls, alkyl carbonyls and aryl carbonyls; and
wherein (i) A is a divalent oligomeric oxyalkylene radical, (ii) Z is a divalent ester radical, or (iii) A is a divalent oligomeric oxyalkylene radical and Z is a divalent ester radical.

2. The compound of claim 1 wherein said A is a divalent oligomeric oxyalkylene radical having the structure:

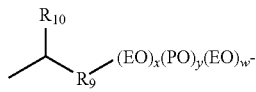

wherein:
EO is ethylene oxide;
PO is propylene oxide;
$R_9$ is a divalent $C_1$-$C_{20}$ alkyl radical;
x, y and w are independently selected from the group consisting of zero and positive integers between 1 and 20;
the sum of x+y+w is equal to or greater than 1; and
$R_{10}$ is either H or a $C_1$-$C_{20}$ alkyl group.

3. The compound of claim 1 wherein Z is a divalent ester radical, said radical having the structure:

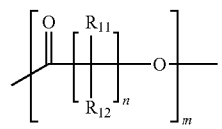

wherein:
$R_{11}$ and $R_{12}$ are independently selected from H or $C_1$-$C_{10}$ alkyl groups;
n is an integer between 1 and 10; and
m is any positive integer between 1 and 20.

4. The compound of claim 2 wherein Z is a divalent ester radical, said radical having the structure:

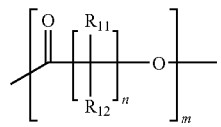

wherein:
$R_{11}$ and $R_{12}$ are independently selected from H or $C_1$-$C_{10}$ alkyl groups;
n is an integer between 1 and 10; and
m is any positive integer between 1 and 20.

5. A composition comprising:
a) an organic material which is subject to oxidative, thermal or light-induced degradation, and
b) at least one compound of formula:

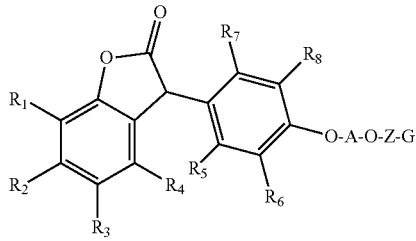

wherein:
$R_1$ and $R_3$ are independently selected from the group consisting of H, $C_1$-$C_{20}$ alkyls, $C_1$-$C_{20}$ cycloalkyls, $C_1$-$C_{20}$ alkoxy groups, $C_7$-$C_{20}$ phenylalkyls, and phenyl groups;
$R_2$ and $R_4$ are each hydrogen;
$R_5$, $R_6$, $R_7$ and $R_8$ are independently selected from the group consisting of H $C_1$-$C_{20}$ alkyl, and $C_1$-$C_{20}$ alkoxy groups;
A is a $C_2$-$C_{20}$ alkylene oxide group or a divalent oligomeric oxyalkylene radical;
Z is a $C_2$-$C_{20}$ alkyl or a divalent ester radical; and
G is an end group selected from the group consisting of H, $C_1$-$C_{10}$ alkyls, alkyl carbonyls and aryl carbonyls; and
wherein (i) A is a divalent oligomeric oxyalkylene radical, (ii) Z is a divalent ester radical, or (iii) A is a divalent oligomeric oxyalkylene radical and Z is a divalent ester radical.

6. The composition of claim 5 wherein A is a divalent oligomeric oxyalkylene radical having the structure:

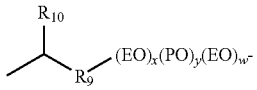

wherein:
EO is ethylene oxide;
PO is propylene oxide;
$R_9$ is a divalent $C_1$-$C_{20}$ alkyl radical;

x, y and w are independently selected from the group consisting of zero and positive integers between 1 and 20;

the sum of x+y+w is equal or greater than 1; and $R_{10}$ is H or a $C_1$-$C_{20}$ alkyl group.

7. The composition of claim 5 wherein Z is a divalent ester radical, said radical having the structure:

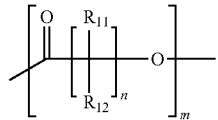

wherein:

$R_{11}$ and $R_{12}$ are independently selected from the group consisting of H and $C_1$-$C_{10}$ alkyl groups;

n is an integer between 1 and 10; and m is any positive integer between 1 and 20.

8. The composition of claim 5 wherein said organic material comprises a synthetic polymer.

* * * * *